(12) United States Patent
Suh

(10) Patent No.: US 9,987,216 B2
(45) Date of Patent: Jun. 5, 2018

(54) PLANT FAT COMPOSITION FOR COSMETIC PREPARATION

(71) Applicant: Nam-su Suh, Seoul (KR)

(72) Inventor: Nam-su Suh, Seoul (KR)

( * ) Notice: Subject to any disclaimer, the term of this patent is extended or adjusted under 35 U.S.C. 154(b) by 0 days. days.

(21) Appl. No.: 15/682,683

(22) Filed: Aug. 22, 2017

(65) Prior Publication Data

US 2018/0110719 A1    Apr. 26, 2018

(30) Foreign Application Priority Data

Oct. 26, 2016  (KR) .......................... 10-2016-0140056

(51) Int. Cl.
*A61K 8/92* (2006.01)
*A61K 8/36* (2006.01)
*A61Q 17/00* (2006.01)
*A61Q 19/00* (2006.01)

(52) U.S. Cl.
CPC .............. *A61K 8/922* (2013.01); *A61K 8/361* (2013.01); *A61Q 17/005* (2013.01); *A61Q 19/00* (2013.01); *A61Q 19/007* (2013.01); *A61K 2800/5922* (2013.01)

(58) Field of Classification Search
None
See application file for complete search history.

(56) References Cited

U.S. PATENT DOCUMENTS

2004/0241254 A1* 12/2004 Kopas .................... A61K 8/922
424/727

* cited by examiner

*Primary Examiner* — Michael Barker
(74) *Attorney, Agent, or Firm* — Lex IP Meister, PLLC

(57) ABSTRACT

The present invention relates to a plant fat composition for cosmetic preparation that has a composition similar to that of a fat in human milk and enables the preparation of cosmetics having excellent moisturizing, antioxidative, anti-inflammatory, and/or antimicrobial effects. The plant fat composition for cosmetic preparation includes, with respect to the total weight of the composition, 24 to 34 wt. % of enzymatically trans-esterified palm oil, 6 to 19 wt. % of coconut oil, 9 to 17 wt. % of sunflower oil, and soybean oil for the rest of the quantity.

6 Claims, 3 Drawing Sheets

PLANT FAT COMPOSITION FOR COSMETIC PREPARATION

TECHNICAL FIELD

The present invention relates to a plant fat composition for cosmetic preparation, and more particularly to a plant fat composition for cosmetic preparation that has a composition similar to that of a fat in human milk and enables the preparation of cosmetics having excellent moisturizing, antioxidative, anti-inflammatory, and/or antimicrobial effects.

BACKGROUND ART

Human skin is composed of three primary layers of tissue: the epidermis, the dermis, and the hypodermis. The epidermis is divided into several sublayers, including stratum corneum, stratum granulosum, stratum spinosum, and stratum basale (from outer most to inner most). Stratum corneum, the outermost layer of the epidermis, functions to form a primary barrier to protect the skin from external physical and chemical stimuli, microbial infection, etc. and to control water evaporation from body fluids for the maintenance of skin homeostasis (Lee, Seung-Heon; Chung, Jun; Ahn, Sung-Gu; Kang, Jin-Soo; Kwon, Oh-Gyu;/Korean Dermatological Association, v. 32(4), pp. 599-603, 1994). The substances that keep the skin soft and tight are mostly dependent upon the water present in the stratum corneum. The water content of the stratum corneum highly depends on the amount of sebum in the epidermis and the aqueous component of the stratum corneum, so-called natural moisturizing factor (NMF) (Spencer T S: "Water and the horny layer", J. Soc. Cosmet. Chem. 27: pp. 63-72, 1976). The sebum covers the skin surface to prevent transepidermal water loss. In contrast, the NMF readily absorbs water and lowers the surface tension of the skin to prevent the repellence of water from the keratinocytes, further making a direct effect on the skin moisturization (Pyo, Kyung-Chan; Kim, Hong-Jik; Kim, Young-Geun;/Korean Dermatological Association, v. 26, pp. 10-15, 1988).

The stratum corneum, once considered to merely have a buildup of dead cells and bodily waste, have various components and functions of its own, which protect the body against external physical and chemical stress, microorganisms, etc. and properly control the water evaporation from body fluids to maintain skin homeostasis. The substances that function to keep the skin soft and tight are mostly dependent upon the water content of the stratum corneum (Choi, Eun-Young;/Korean Dermatological Association, v. 4, No. 2, pp. 2).

The conventional moisturizer most popular as a solution to this problem is polyhydric alcohol, such as glycerin, propylene, sorbitol, etc. Microbe-derived sodium hyaluronate is also in use as a moisturizer. As people today use a lot of chemical artificial ingredients, their skin is susceptible to dehydration, irritations, allergies, etc.

Further, a succession of recent detections of toxic substances from the disinfectants for humidifiers results in a phobia about chemical products.

Korean Patent Publication No. 10-2004-0021695 discloses "a moisturizer and a cosmetic material and a topical formulation including the same", which patent provides a moisturizer having excellent moisture retention characteristic and high stability at high temperatures of 40° C. or above, and a cosmetic material and a topical formulation including the moisturizer. For this purpose, the cited patent describes a moisturizer and a cosmetic material and a topical formulation including the same, which moisturizer comprises: (a) an ester compound composed of at least one of glycerin and its condensate, a linear-chain saturated fatty acid having 16 to 28 carbon atoms and a saturated aliphatic dibasic acid having 16 to 28 carbon atoms, where the ester compound has hydroxyl groups half as many as the total number of the hydroxyl groups in the at least one of the glycerin and its condensate; (b) an aqueous dihydric alcohol; and (c) an aqueous, at least trihydric alcohol.

Korean Patent Publication No. 10-2013-0134803 discloses "a moisturizing cosmetic composition comprising a propolis-containing nanovesicle", where the moisturizing cosmetic composition includes a defined amount of the propolis-containing nanovesicle.

Korean Patent Publication No. 10-2014-0117862 is directed to "an oil-in-water type silicone-emulsified moisturizing cosmetic composition having a transparent property, a preparation method for the same, and a moisturizing cosmetic containing the same". The cited patent describes an oil-in-water type silicone-emulsified moisturizing cosmetic composition that contains a polyol-based moisturizing component and an aqueous moisturizing component at high concentration to maximize the skin moisturization and promotes the compatibility between silicone and the aqueous phase including the polyol-based moisturizing component and the aqueous moisturizing component both contained at high concentration not only to improve the finishing tough overcoming sticky sensation and poor softness caused by the presence of the high-concentration polyol-based moisturizing component but also to attain a transparent property.

Korean Registered Patent Publication No. 10-1152315 (published on Jun. 11, 2012) discloses "a method for preparing a fat composition for chocolate and confectionary using enzymatic trans-esterification".

Accordingly, there is an urgent demand for developing a plant fat composition for cosmetic preparation that is available for the consumers with a safe conscience and enables the preparation of cosmetic materials using eco-friendly, nature-originated ingredients to cope with the environmental factors such as fine dust and particularly having excellent moisturizing, antioxidative and/or antimicrobial effects.

DISCLOSURE OF INVENTION

It is an object of the present invention to provide a plant fat composition for cosmetic preparation that has a composition similar to that of a fat in human milk and enables the preparation of cosmetics having excellent moisturizing, antioxidative, anti-inflammatory, and/or antimicrobial effects.

In accordance with the present invention, there is provided a plant fat composition for cosmetic preparation including, with respect to the total weight of the composition, 24 to 34 wt. % of enzymatically trans-esterified palm oil, 6 to 19 wt. % of coconut oil, 9 to 17 wt. % of sunflower oil, and soybean oil for the rest of the quantity.

An enzyme used for esterification of the enzymatically trans-esterified palm oil may be derived from *Rhizomucor miehei*.

The sunflower oil may contain 80 wt. % of oleic acid.

Effects of the Invention

The present invention has an effect to provide a plant fat composition for cosmetic preparation and a cosmetic preparation including the same, where the plant fat composition for cosmetic preparation has a composition similar to that of a fat in human milk and enables the preparation of cosmetics having excellent moisturizing, antioxidative, anti-inflammatory, and/or antimicrobial effects.

BEST MODES FOR CARRYING OUT THE INVENTION

Figure 1:
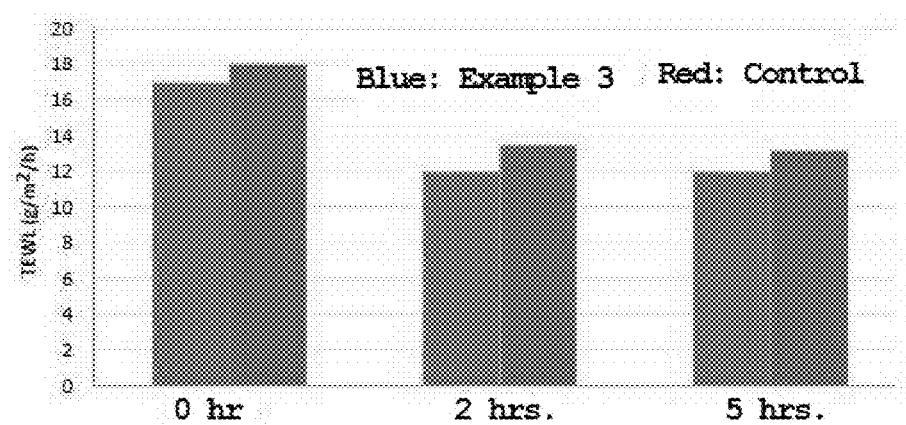
FIG. 1 is a graph showing the transepidermal water loss after treatment with the plant fat composition of Example 3 according to the present invention and a plant-derived squalane product used as a control.

Hereinafter, a detailed description will be given as to the specific embodiments of the present invention with reference to the accompanying drawings.

The present invention provides a plant fat composition for cosmetic preparation comprising, with respect to the total weight of the composition, 24 to 45 wt. % of enzymatically trans-esterified palm oil, 5 to 20 wt. % of coconut oil, 13 to 20 wt. % of sunflower oil, and soybean oil for the rest of the quantity.

More preferably, the present invention provides a plant fat composition for cosmetic preparation comprising, with respect to the total weight of the composition, 24 to 34 wt. % of enzymatically trans-esterified palm oil, 6 to 19 wt. % of coconut oil, 9 to 17 wt. % of sunflower oil, and soybean oil for the rest of the quantity. Particularly, the present invention is directed to a plant fat composition having eco-friendly nature-originated ingredients, and the plant fat composition comprises, with respect to the total weight of the composition, 30 wt. % of enzymatically trans-esterified palm oil, 10 wt. % of coconut oil, 13 wt. % of sunflower oil, and soybean oil for the rest of the quantity. The plant fat composition has a composition similar to that of the fat in human milk, displays an extraordinarily excellent moisturizing effect and good safety like the fat in human milk due to its similarity in composition to the fat in human milk, and also offers good antioxidative, anti-inflammatory, and/or antimicrobial effects.

98 percent of the fat in human milk is triglycerides, which are composed of three fatty acids bound to a glycerol backbone at positions sn-1, sn-2 and sn-3 (Giovannini, M., E. Riva, and C. Agostoni, Fatty acids in pediatric nutrition. Pediatr Clin North Am, 1995. 42(4): p. 861-77.). The principal saturated fatty acid of human milk, palmitic acid, accounts for 17 to 25% of the human milk fat, and 70% of the palmitic acid in human milk is esterified at position sn-2 of triglycerides (Breckenridge, W. C., L. Marai, and A. Kuksis, Triglyceride structure of human milk fat. Can J Biochem, 1969. 47(8): p. 761-9. And Jensen, R. G., Lipids in human milk. LIPIDS, 1999. 34(12): p. 1243-71.). It is therefore impossible to prepare a fatty acid composition similar to human milk merely by mixing general plant fats together.

The plant fat composition according to the present invention uses palm oil prepared by trans-esterification particularly with the help of an enzyme in order to obtain a composition similar to that of the fat in human milk. There are two trans-esterification mechanisms: chemical trans-esterification and enzymatic trans-esterification. The chemical trans-esterification forms three byproducts at high temperature by using sodium methoxide. In contrast, the enzymatic trans-esterification is a simple ester-preparation process advantageously accomplished at low cost and without byproducts. The enzymatic trans-esterification is a catalytic reaction that is accomplished by mixing two oils, the one of which is liquid and the other is solid at room temperature in most cases, and adding the mixture of oils to an enzyme-containing culture medium. In the enzymatic trans-esterification, there occurs a rearrangement of the fatty acids bound to the glycerol backbone of the triglycerides. Namely, the positions of the fatty acids are shifted to the positions sn-1 and sn-3 through the reaction between the oils and the enzyme. In the case of a trans-esterification of palmitic acid and oleic acid with the help of an enzyme, the fatty acids on the glycerol backbone of triglycerides are naturally rearranged to another positions, only to form eight new different triglycerides as follows:

| | |
|---|---|
| C16:0 (palmitic acid) | C16:0 (palmitic acid) |
| C18:1 (oleic acid) | C16:0 (palmitic acid) |
| C18:1 (oleic acid) | C18:1 (oleic acid) |
| C16:0 (palmitic acid) | C16:0 (palmitic acid) |
| C18:1 (oleic acid) | C16:0 (palmitic acid) |
| C16:0 (palmitic acid) | C16:0 (palmitic acid) |
| C18:1 (oleic acid) | C18:1 (oleic acid) |
| C18:1 (oleic acid) | C16:0 (palmitic acid) |
| C16:0 (palmitic acid) | C16:0 (palmitic acid) |
| C18:1 (oleic acid) | C18:1 (oleic acid) |
| C16:0 (palmitic acid) | C18:1 (oleic acid) |
| C18:1 (oleic acid) | C18:1 (oleic acid) |

The enzymatically trans-esterified palm oil is obtained by performing a trans-esterification reaction, particularly an enzyme-catalyzed trans-esterification reaction of palm oil. Palm oil is an oil derived from the pulp of the fruit of the oil palm, *Elaeis quineensis* Jacq. The fruit of the oil palm consists of skin, pulp and seed, the pulp between the skin and the seed. The fatty acid components of the palm oil consist of 1 to 6% myristic acid, 32 to 43% palmitic acid, 2 to 6% stearic acid, 40 to 52% oleic acid, 5 to 11% linoleic acid, and less than 1% unsaponifiable substances. Decolorization of the palm oil can be easily accomplished by addition of an orange-colored oil containing carotene, oxidation through air intake, or treatment with an oxidant such as hydrogen peroxide, etc. The palm oil mostly contains a large quantity of free fatty acids, occasionally more than 50% of free acids. Its uses are for the manufacture of soaps, candle, etc. and edible purpose. Particularly, the present invention is characterized by changing the composition of the fatty acids in the palm oil through esterification, specifically trans-esterification. In the plant fat composition of the present invention, the content of the enzymatically trans-esterified palm oil ranges from 24 wt. % to 34 wt. % with respect to the total weight of the composition. As the plant fat composition of the present invention becomes similar in composition to the fat in human milk, it has good moisturizing, antioxidative, anti-inflammatory, and/or antimicrobial effects. When the content of the enzymatically trans-esterified palm oil is out of the defined range, it means that the fat composition differs from that of the fat in human milk, so the fat composition fails to attain excellent moisturizing, antioxidative, anti-inflammatory, and/or antimicrobial effects.

In particular, the enzyme used for the trans-esterification in the enzymatically trans-esterified palm oil may be derived from *Rhizomucor miehei*.

The coconut oil is an oil compressed from the decoated coconuts harvested from the coconut palm (*Cocos Nucifera* Linne). It is commonly used in the cosmetic formulations, including fragrance, skin conditioner (as a vapor retarder, etc.), hair conditioner, or the like. In the plant fat composition of the present invention, the content of the coconut oil ranges from 6 wt. % to 19 wt. % with respect to the total weight of the composition. As the plant fat composition of the present invention becomes similar in composition to the fat in human milk, it attains good moisturizing, antioxidative, anti-inflammatory, and/or antimicrobial effects. When the content of the coconut oil is out of the defined range, the fat composition differs in composition from the fat in human milk, so the fat composition fails to have good moisturizing, antioxidative, anti-inflammatory, and/or antimicrobial effects.

The sunflower oil is a semidrying oil obtained from the seeds of sunflower (*Helianthus annuus* L. (*chrysanthemum*)). Its principal ingredient is triglyceride consisting of linoleic acid (60 wt. %) and oleic acid. It is a light-tasted oil that is a good ingredient for sauce and salad dressing and has good keeping qualities without being overshadowed by other tastes. As for the fatty acid composition, the sunflower oil contains 8.7 to 14.2 wt. % of saturated acids (e.g., palmitic acid, stearic acid and arachic acid), 14.1 to 43.1 wt. % of oleic acid, 44.2 to 75.4 wt. % of linoleic acid, and less than 1.5 wt. % of unsaponifiable components, so it is suitable for edible purposes as a liquid-state oil. The sunflower oil has various applications like salad dressing oil, margarine (if hydrogenated), and shortening oil. In the plant fat composition of the present invention, the content of the sunflower oil ranges from 9 wt. % to 17 wt. % with respect to the total weight of the composition. As the plant fat composition of the present invention becomes similar in composition to the fat in human milk, it attains good moisturizing, antioxidative, anti-inflammatory, and/or antimicrobial effects. When the content of the sunflower oil is out of the defined range, the fat composition differs in composition from the fat in human milk, so the fat composition fails to have good moisturizing, antioxidative, anti-inflammatory, and/or antimicrobial effects.

Preferably, the content of olefin acid in the sunflower oil is 80 wt. %.

The soybean oil is a semidrying (or drying) oil obtained from the seeds of the soybean (*Glycine max* Merrill) through compression or solvent extraction. It is characterized by its relatively high content (ranging from 1.5 wt. % to 2.5 wt. %) of ingredients (primarily phosphatides) other than glycerides. The plant fat composition is also composed of fatty acids: 14 to 16 wt. % of saturated acids, 16 to 32 wt. % of oleic acid, 47 to 61 wt. % of linoleic acid, 6 to 8 wt. % of linolenic acid, 0.5 to 1.6 wt. % of unsaponifiable substances, which include phytosterol, as a principal component, or stigmasterol. Unrefined soybean oil is yellowish brown with an unpleasant odor, whereas refined soybean oil is odorless and tastes good. The soybean oil is distinctly inferior in drying properties to flaxseed oil, with its dry film weaker than that of flaxseed oil. Oil yield extracted from the soybean is sufficiently large, so the soybean oil is a significant industrial raw material, mostly purified and used for edible purpose. It is also used in hardened oil, quenching oil, boiled oil, and so forth. In the plant fat composition of the present invention, the content of the fatty acid components accounts for the rest of the plant fat composition with respect to the total weight of the composition. As the plant fat composition of the present invention becomes similar in composition to the fat in human milk, it attains good moisturizing, antioxidative, anti-inflammatory, and/or antimicrobial effects. When the content of the fatty acid components is out of the defined range, the fat composition differs in composition from the fat in human milk, so the fat composition fails to have good moisturizing, antioxidative, anti-inflammatory, and/or antimicrobial effects.

The fatty acid composition in the plant fat composition of the present invention is similar to that of Korean's human milk fat, since it is comprised of: up to 11.0 wt. % of C12 (lauric acid)+C14 (myristic acid), 16.0 to 24 wt. % of C16 (palmitic acid), 34 to 42 wt. % of C18-1 (oleic acid), and at least 3.0 wt. % of C18-3 (linoleic acid), and the content of sn-2 palmitic acid at position sn-2 of the triglyceride ranges from 13.2 wt. % to 17.6 wt. %, which makes up 40 wt. % of the palmitic acid (Korean Society of Pediatric Endocrinology, *Annals of Pediatric Endocrinology & Metabolism*, Vol. 9, no. 2; pp 175. 2004).

Table 1 presents a comparison in the fatty acid content between the plant fat composition of the present invention and the Korean's human milk composition.

TABLE 1

| Fatty acid | Plant fat composition of the present invention | Korean's human milk composition |
| --- | --- | --- |
| C12:0 + C14:0 | Up to 11.0 wt. % | 9.8 to 17.2 wt. % |
| C16:0 | 16.0 to 24.0 wt. % | 18.9 to 25.1 wt. % |
| C18:1 | 34.0 to 42.0 wt. % | 21.8 to 32.6 wt. % |
| C18:3 | at least 3.0 wt. % | 1.4 to 3.0 wt. % |

Skin moisturization means preventing evaporation of water and attracting water vapor from the air as well. The plant fat composition of the present invention aims at making a cosmetic preparation from nature-originated plant oils that has good safety and excellent skin moisturizing function, anti-oxidative function, and antimicrobial function, where the skin moisturizing function involves covering the surface of the skin to prevent transepidermal water loss and to keep the skin from drying, preventing the acceleration of the skin aging and controlling the water content of the skin (skin's hydration); the anti-oxidative function includes scavenging lypoperoxide and free radicals to prevent the skin aging; and the antimicrobial function is protecting the skin against germs or other microorganisms.

Hereinafter, a description will be given as to the preferred examples of the present invention and comparative examples.

The following examples are given for the illustration of the present invention only and not construed to limit the scope of the present invention.

Example 1

A plant fat composition for cosmetic preparation according to the present invention was prepared by mixing, with respect to the total weight of the composition, 45 wt. % of enzymatically trans-esterified palm oil, 5 wt. % of coconut oil, 18 wt. % of sunflower oil (containing at least 80% oleic acid), and 32 wt. % of soybean oil. In all the examples of the present invention, the enzymatically trans-esterified palm oil used an enzyme derived from *Rhizomucor miehei* in the trans-esterification reaction.

Example 2

A plant fat composition for cosmetic preparation according to the present invention was prepared by mixing, with respect to the total weight of the composition, 35 wt. % of enzymatically trans-esterified palm oil, 20 wt. % of coconut oil, 18 wt. % of sunflower oil (containing at least 80% oleic acid), and 27 wt. % of soybean oil.

Example 3

A plant fat composition for cosmetic preparation according to the present invention was prepared by mixing, with respect to the total weight of the composition, 30 wt. % of enzymatically trans-esterified palm oil, 10 wt. % of coconut oil, 13 wt. % of sunflower oil (containing at least 80% oleic acid), and 47 wt. % of soybean oil.

Experimental Example 1

:Transepidermal Water Loss

The skin barrier is a protective skin layer designed to prevent the loss of water out of skin and to protect the skin against external environments, that is, preventing the entrance of germs or irritants from UV radiations, or the like. The transepidermal water loss (TEWL) is an essential physiological indicator in the damage and recovery process of the skin barrier. Accordingly, a Tewanmeter that directly measures the physiological function of the epidermis dynamically varying under skin irritation, acute or chronic dermatitis, or dry skin condition can be used to obtain results rapidly and to properly reflect the physiological characteristics of the skin exposed to the open air.

As the water content of skin is measured in the first stage of the TEWL evaluation, an ice condenser type AquaFlux (Biox, the United Kingdom) instrument was used as a means for long-term measurement of a constant water loss from evaporation for up to 90 seconds without being affected by the environment. All the experiments were performed in a room with the temperature and humidity conditions under control.

[Experimental Results]

FIG. 1 shows the transepidermal water loss of the plant fat composition of Example 3 according to the present invention and a control, that is, a plant-derived squalane product (Phyto Squalene). Squalane is a representative raw material of cosmetic formulations that has a very good skin moisturizing effect and helps skin protection. The plant-derived squalane is generally used in the manufacture of cosmetics as a raw material having the best moisturizing (emollient) effect. Plant-derived squalane is an oil extracted from olive oil, whereas animal-derived squalane is an oil extracted from the liver oil of deep-sea sharks and also found in human skin at around 3 to 4%.

The difference between the emollient and the moisturizer lies in the solubility to water. For oils, the moisturizing effect is also called "emollient effect".

100 µl of each product was applied to the skin on the inner side of the upper arm and kept absorbed into the skin for 5 minutes. The transepidermal water loss was then measured at predetermined intervals.

As a result, as shown in FIG. 1, the transepidermal water loss was decreased by 20% or greater from the initial value in both of the two test groups. But, the plant fat composition of the present invention had the lower transepidermal water loss than the control. The lower transepidermal water loss means the less water loss out of skin due to the better skin barrier function. As the higher transepidermal water loss describes the higher tendency to dry skin, it is explicitly considered that the plant fat composition of the present invention is superior in the moisturizing (emollient) effect to the plant-derived squalane.

In addition, all the test subjects (n=6) had no irritation to both the plant fat composition of the present invention and the plant-derived squalane.

Experimental Example 2

:Antioxidative Effect
Test Material and Method
—Characteristics of Testing

DPPH (2,2-diphenyl-1-picryl-hydrazyl) is a purple-colored stable free radical substance that receives hydrogens from an antioxidant to undergo decolorization. Upon exposure to an antioxidant, the DPPH acts as a donor of electrons to the antioxidant and becomes removed of free radicals, resulting in decolorization, which makes it possible to evaluate the radical-scavenging activity.

Vitamin E (acetate) was used as a control.
—Test Procedures (a) Prepare a 0.2 mM DPPH reagent dissolved in n-hexane.

(b) Prepare test samples by concentration.

(c) Add 100 µl of the reagent and 100 µl of each sample in four wells of a 96-well test plate.

(d) Add 100 µl of the reagent and 100 µl of a solvent in four wells to remove the blank value.

(e) Kept in the dark for 30 minutes at the room temperature.

(f) Measure the absorbance at 540 nm with an ELISA reader (TECAN microplate reader).
—Test Results
Analysis Method (Calculation Method)

DPPH radical scavenging ability (%)=[1−(absorbance of sample/absorbance of blank)]×100

Figure 2:
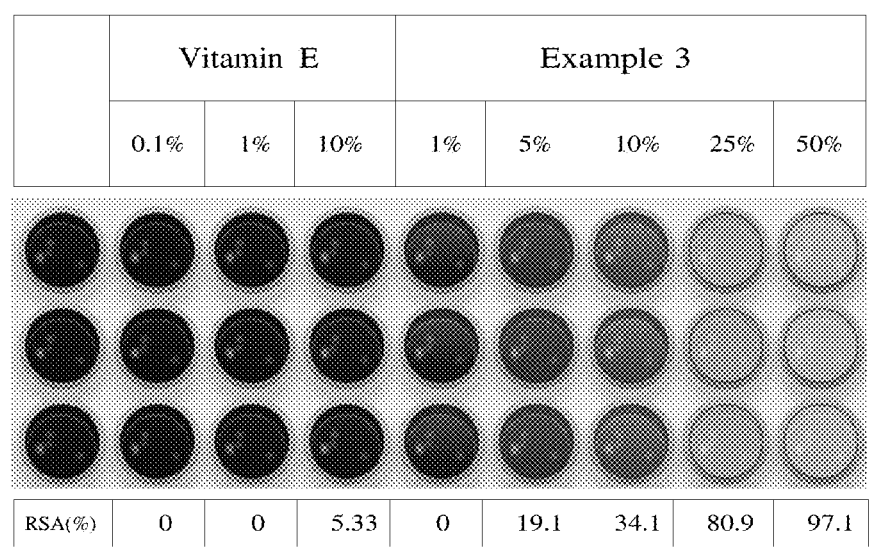
FIGS. 2 and 3 are diagrams showing the radical scavenging activities of the plant fat composition of Example 3 according to the present invention and vitamin E used as a positive control.
Figure 3:
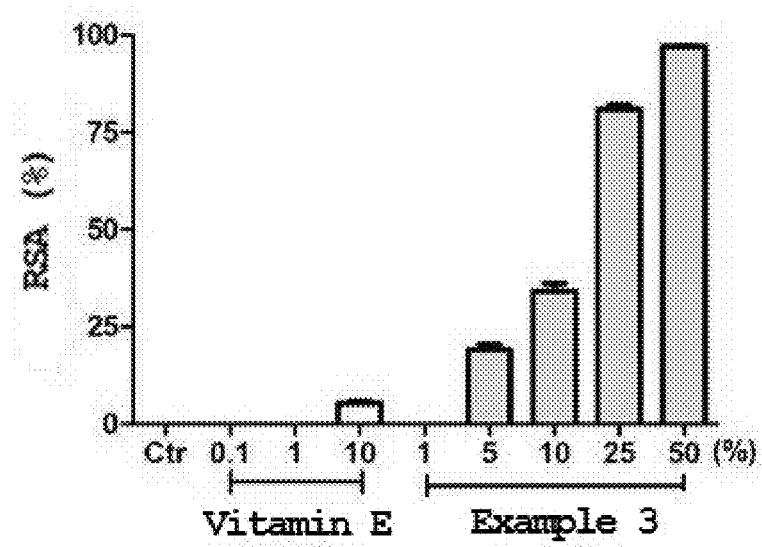

The averaged radical scavenging ability is presented in FIGS. 2 and 3. For the vitamin E used as a positive control, the radical scavenging activity began to appear as 5% at Vitamin E concentration of 10%. On the other hand, the Example 3 of the present invention displayed the radical scavenging activity at concentration of 5% or higher, but not at concentration of 1%, explicitly showing that the radical scavenging activity was increased in a concentration-dependent manner. In addition, the Example 3 of the present invention had the higher radical scavenging activity than Vitamin E used as a control by about 30%.

Conclusion

Vitamin E used as a positive control is known to have an antioxidative effect. A DPPH analysis to evaluate the radical scavenging activity in the antioxidation test showed that the plant fat composition of the Example 3 according to the present invention had the higher radical scavenging activity than Vitamin E. It is therefore possible to expect a high antioxidative effect from the raw material.

Experimental Example 3

:Anti-inflammatory Effect

To evaluate the anti-inflammatory effect of the plant fat composition according to the present invention, each ear of a mouse was cleansed with ethanol prior to the application of the specimen. The left ear was a target region of the control, and the right ear was a target region of the test specimen. 20 µl of the specimen was daily applied to each ear for four days. In one hour after the last application, ethanol was applied to the left ear and arachidonic acid was applied to the right ear at 2 mg/ear. In one hour, the extent of ear edema on both ears was measured in micrometers repeatedly three times.

The anti-inflammatory effect was evaluated in terms of the degree of edema inhibition (%) with reference to the group treated with arachidonic acid. The degree of edema inhibition was determined according to the following equation. The calculation results are presented in Table 2.

$$\text{Edema inhibition (\%)} = ((A-B)/A) \times 100$$

In this equation, A is the average thickness of the ears treated with the control (=the thickness of the ear treated with arachidonic acid−the thickness of the ear not treated); and B is the average thickness of the ears treated with the specimen (=the thickness of the ear treated with the specimen−the thickness of the ear not treated).

TABLE 2

| Specimen | Concentration (%) | Solvent | Thickness of ear (μm) Before treatment | Thickness of ear (μm) After treatment | Inhibition rate (%) |
|---|---|---|---|---|---|
| Arachidonic acid | 2 mg/ear | Ethanol | 290 | 542 | — |
| Example 1 | 0.5 | | 290 | 505 | 14.7 |
| | 1.0 | | 276 | 487 | 16.3 |
| | 2.0 | | 285 | 493 | 17.5 |
| Example 2 | 0.5 | | 289 | 487 | 21.4 |
| | 1.0 | | 291 | 485 | 23.0 |
| | 2.0 | | 293 | 483 | 24.6 |
| Example 3 | 0.5 | | 278 | 468 | 24.6 |
| | 1.0 | | 287 | 472 | 23.0 |
| | 2.0 | | 293 | 471 | 29.4 |

As can be seen from Table 2, the plant fat compositions of the present invention had the higher anti-inflammatory effect than arachidonic acid. Particularly, the composition of Example 3 is superior in anti-inflammatory effect to those of Examples 1 and 2.

Experimental Example 4

:Antimicrobial and Antifungal Effect

The compositions of the Examples 1, 2 and 3 according to the present invention were measured in regards to the antimicrobial and antifungal effect.

The agar disc-diffusion method using a paper disc was adopted in the antimicrobial and antifungal test. Inoculation of the microbes in question is made with 100 ml of a broth culture and the microbes were activated through incubation at 37° C. for 48 hours. A top agar (0.75% agar) plate was inoculated with 100 μl of the microbe-incubating broth culture (107 to 108 cfu/ml), so the broth culture was applied onto the plate. 20 μl of a test specimen was applied to each sterile paper disc, which was then dried out and placed on the plate. After the completion of 36-hour incubation, the diameter of the clear zone formed around the agar plate was measured to evaluate the antimicrobial and antifungal effect.

The microbial pathogens as used herein include: *Candida albicans* (ATCC 10259), *Escherichia coli* (ATCC 25922), *Staphylococcus aureus* (ATCC 29737), and *Bacillus subtilis* (ATCC 6633). The culture for the growth of microbes was typically nutrient agar or trypticase soy agar (Difco). The microbe-specific incubation conditions are presented in Table 3. The test results are shown in Table 4.

TABLE 3

| No. | Microorganism | Culture medium | Type |
|---|---|---|---|
| 1 | *Candida albicans* | General agar | Aerobic |
| 2 | *Escherichia coli* | Trypticase soy agar | Aerobic |
| 3 | *Staphylococcus aureus* | General agar | Aerobic |
| 4 | *Bacillus subtilis* | General agar | Aerobic |

TABLE 4

| Microorganism | Concentration (wt. %) | | 1.0 | 3.0 | 5.0 | 10.0 |
|---|---|---|---|---|---|---|
| *Candida albicans* | Example | 1 | 6 | 7 | 8 | 10 |
| | | 2 | 8 | 9 | 10 | 14 |
| | | 3 | 8 | 10 | 11 | 16 |
| *Escherichia coli* | Example | 1 | 6 | 7 | 9 | 9 |
| | | 2 | 8 | 10 | 11 | 14 |
| | | 3 | 9 | 10 | 12 | 16 |
| *Staphylococcus aureus* | Example | 1 | 6 | 7 | 8 | 10 |
| | | 2 | 8 | 10 | 11 | 16 |
| | | 3 | 8 | 10 | 14 | 16 |
| *Bacillus subtilis* | Example | 1 | 6 | 7 | 8 | 10 |
| | | 2 | 8 | 10 | 11 | 14 |
| | | 3 | 9 | 10 | 12 | 15 |

As can be seen from Table 4, the compositions of the Examples according to the present invention exhibited an excellent antimicrobial function. Particularly, the composition of the Example 3 was superior in the antimicrobial and antifungal effect to those of the Examples 1 and 2, and the antimicrobial and antifungal effect varied in the concentration-dependent manner.

For reference, Table 5 presents the results of the research on the antimicrobial lipids present in human milk as conducted by Kabara and his associates (Kabara J J. Lipids as host-resistance factors of human milk. *Nutr. Rev.* 1980; pp 1475. 38:65-73.) et al.

TABLE 5

| Antimicrobial lipids | | |
|---|---|---|
| Fatty acid | Monoglyceride | Carbon atoms:double bonds |
| Caprylic | Monocaprylin | 8:0 |
| Capric | Monocaprin | 10:0 |
| Undecylenic | — | 11:1 |
| Lauric | Monolaurin | 12:1 |
| Myristic | Monomyristin | 14:0 |
| Palmitoleic | Monopalmitolein | 16:1Δ9 |
| Sapienic | — | 16:1Δ6 |
| Oleic | Monoolein | 18:1 |
| Linoleic | — | 18:2 |
| Linolenic | — | 18:3 |
| arachidonic | — | 20:4 |

Experimental Example 5

:Safety

Fatty acids, such as oleic acid, lauric acid, palmitic acid, myristic acid, stearic acids, etc., are widely used in cosmetic formulations. A series of tests using human and animal subjects in regards to skin irritation, skin sensitization, photo-sensitization, and ocular irritation make a conclusion that oleic acid, lauric acid, palmitic acid, myristic acid, and stearic acid are all safe in use for cosmetic formulations (*Journal of the American College of Toxicology*. Vol. 6, pp 373-389. No. 3, 1987).

What is claimed is:

1. A plant fat composition for cosmetic preparation comprising, with respect to the total weight of the composition, 24 to 34 wt. % of enzymatically trans-esterified palm oil, 6 to 19 wt. % of coconut oil, 9 to 17 wt. % of sunflower oil, and soybean oil for the rest of the quantity.

2. The plant fat composition for cosmetic preparation as claimed in claim 1, wherein an enzyme used for esterification of the enzymatically trans-esterified palm oil is derived from *Rhizomucor miehei*.

3. The plant fat composition for cosmetic preparation as claimed in claim 1, wherein the sunflower oil contains 80 wt. % of oleic acid.

4. A cosmetic preparation comprising the plant fat composition for cosmetic preparation as claimed in claim 1 as an active ingredient.

5. A cosmetic preparation comprising the plant fat composition for cosmetic preparation as claimed in claim 2 as an active ingredient.

6. A cosmetic preparation comprising the plant fat composition for cosmetic preparation as claimed in claim 3 as an active ingredient.

* * * * *